US00PP34398P3

(12) United States Plant Patent
Dale et al.

(10) Patent No.: US PP34,398 P3
(45) Date of Patent: Jul. 5, 2022

(54) BANANA PLANT NAMED 'QCAV-4'

(50) Latin Name: *Musa acuminata*
Varietal Denomination: 'QCAV-4'

(71) Applicant: Queensland University of Technology, Brisbane (AU)

(72) Inventors: James Dale, Brisbane (AU); Robert Harding, Brisbane (AU); Harjeet Khanna, Brisbane (AU); Anthony James, Brisbane (AU); Jennifer Kleidon, Brisbane (AU); Mark Smith, Darwin (AU); Upendra Shekhawat, Brisbane (AU)

(73) Assignee: Australian Banana Research Pty Ltd., Footscray (AU)

( * ) Notice: Subject to any disclaimer, the term of this patent is extended or adjusted under 35 U.S.C. 154(b) by 0 days.

(21) Appl. No.: 16/873,740

(22) Filed: Jun. 19, 2020

(65) Prior Publication Data

US 2021/0400858 P1 Dec. 23, 2021

(51) Int. Cl.
*A01H 5/08* (2018.01)
*A01H 6/00* (2018.01)

(52) U.S. Cl.
USPC ..... Plt./160
CPC ..... *A01H 6/00* (2018.05)

(58) Field of Classification Search
USPC ..... Plt./160
CPC ..... A01H 6/00
See application file for complete search history.

(56) References Cited

U.S. PATENT DOCUMENTS 6,133,035 A * 10/2000 Engler et al. ..... 435/419
7,601,887 B2 * 10/2009 Dale et al. ..... 800/279

OTHER PUBLICATIONS

"Transgenic Cavendish bananas with resistance to Fusarium wilt tropical race 4," Dale et al., Nature Communications,8: 1496, |DOI: 10.1038/s41467-017-01670-6/www.nature.com/naturecommunications, pp. 1-8, published Nov. 14, 2017.*
Plant Variety Gazette of the Philippines Plant Variety Protection Office, vol. 32, Jun. 28, 2020 (10 pages). See p. 4.
Plant Varieties Journal, vol. 33, No. 3, Nov. 20, 2020 (416 pages). See p. 10.
Declaration of Timothy Fitzgerald, Ph.D., executed on Dec. 11, 2021.

* cited by examiner

*Primary Examiner* — Anne Marie Grunberg
(74) *Attorney, Agent, or Firm* — Klarquist Sparkman, LLP

(57) ABSTRACT

A new banana cultivar 'QCAV-4' is provided that, when under significant disease pressure, remains largely free from infection by *Fusarium* wilt tropical race 4 (TR4). In the absence of such significant disease pressure, 'QCAV-4' appears to be essentially phenotypically identical to the wild type parent Cavendish Grand Nain. This includes in relation to immature and mature plant characteristics, fruit characteristics, and yield.

12 Drawing Sheets

Specification includes a Sequence Listing.

Latin name of the genus and species of the plant claimed: *Musa acuminata.*

Variety denomination: 'QCAV-4'.

BACKGROUND OF THE INVENTION

The present invention relates to a new and distinct cultivar of banana plant named 'QCAV-4'. The new plant resulted from transformation of parent Cavendish Grand Nain (unpatented) by T-DNA insertion and selection. A resulting transgenic plant named 'QCAV-4' was selected when growing in a cultivated area in Lambells Lagoon, Northern Territory, Australia.

BRIEF SUMMARY OF THE INVENTION

'QCAV-4' is a transgenic cultivar produced from Cavendish Grand Nain. For initial transformation, embryogenic cell suspensions (ECS) were generated from immature male flowers from the bell (flower) of Cavendish Grand Nain. The bells were collected in North Queensland, Australia and indexed for virus infection. The ECS were transformed using *Agrobacterium* mediated transformation. The transformation cassette included a selectable marker gene, neomycin phosphotransferase (NPT II). The resistance gene was a gene isolated from *Musa acuminata* subsp. *malaccensis* which is resistant to *Fusarium* wilt tropical race 4 (TR4). The resistance gene was under the control of the nos promoter. Potentially transformed cells were placed on kanamycin to select NPT II resistant cells. These were then regenerated into whole plantlets and multiplied. Presence of the transgenes were confirmed by PCR. Multiplied plantlets were transferred to a farm in Lambells Lagoon, Northern Territory, Australia and acclimatized in a screenhouse. These plants together with appropriate controls were planted into a plot where Cavendish bananas had been previously grown and had been severely affected by *Fusarium* wilt TR4. The plot was "seeded" further with pseudostem segments from infected Cavendish plants. Plants were regularly inspected for TR4 symptoms over a three-year period. Multiple independent transformed lines demonstrated strong resistance to TR4 as compared to the parental Cavendish Grand Nain, which is highly susceptible. Morphological characteristics of plants and fruit were assessed, bunch weight was measured, and molecular analysis was performed. One line was selected based on morphological and molecular analysis, and named 'QCAV-4'.

The 'QCAV-4' cultivar is distinguished from other banana varieties, including the parent, by having a strong resistance phenotype to *Fusarium* wilt tropical race 4 (TR4). It is substantially phenotypically identical to its parent in the absence of disease pressure.

Asexual reproduction of 'QCAV-4' by tissue culture in Brisbane City, Queensland, Australia in combination with field assessment in Lambells Lagoon, Northern Territory, Australia, shows that the foregoing characteristic resistance to Fusarium wilt TR4 reproduces true to type.

The following detailed description concerns progeny lines asexually propagated from the original line by tissue culture.

Figure 1A:
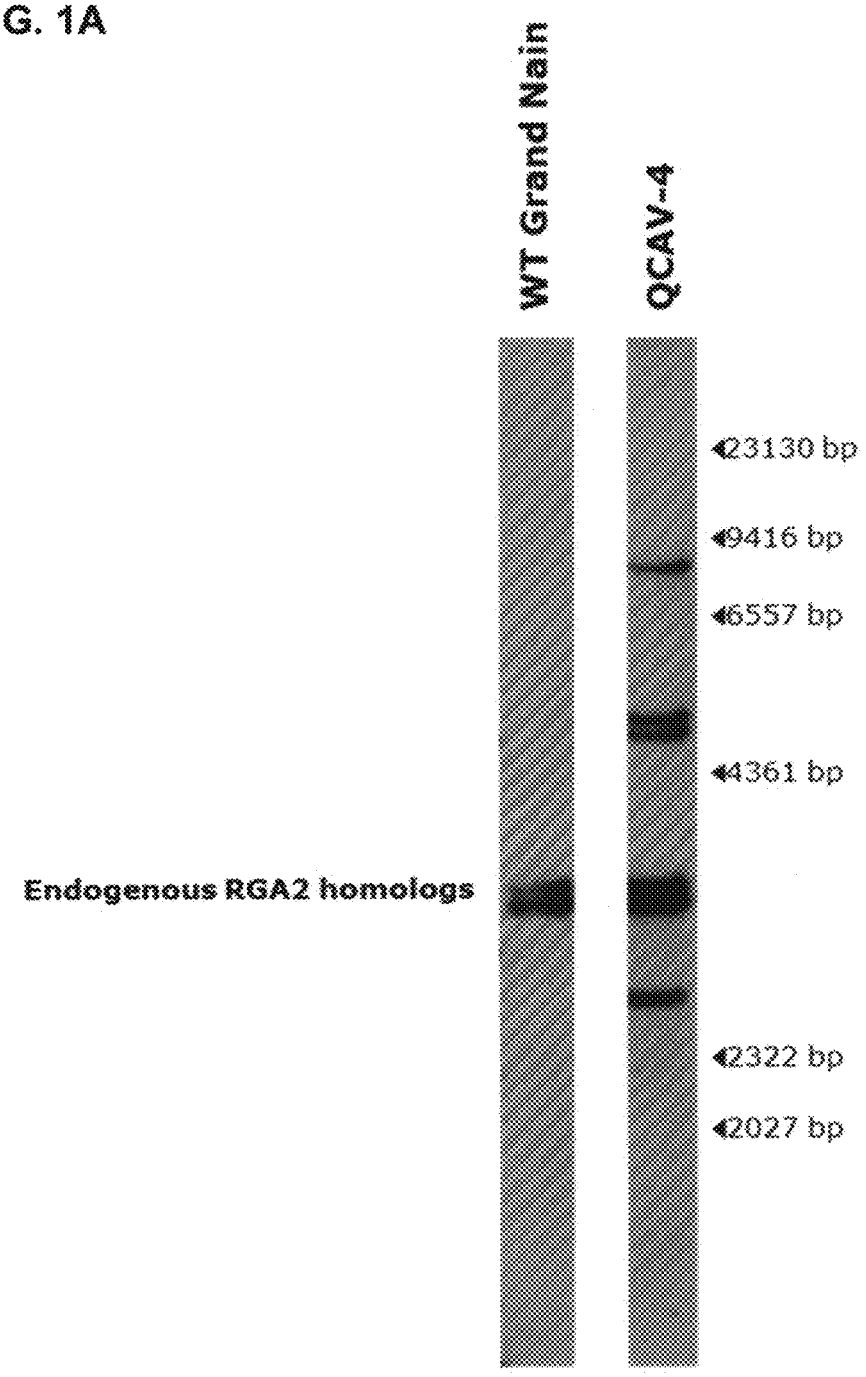
FIG. 1A is a digital image of Southern blot analysis of wild type Cavendish Grand Nain (parent) and 'QCAV-4', showing endogenous RGA2 copies and transgenic RGA2 insertions.

The colors of an illustration of this type may vary with lighting and other conditions under which conditions and, therefore, color characteristics of this new cultivar should be determined with reference to the observations described herein, rather than from these illustrations alone.

SEQUENCE LISTING

The amino acid sequences listed in the accompanying sequence listing are shown using standard three letter code for amino acids, as defined in 37 C.F.R. 1.822. The Sequence Listing is submitted as an ASCII text file, created on Dec. 14, 2021, 12 KB, which is incorporated by reference herein. In the accompanying sequence listing:

SEQ ID NOs: 1-7 are new ORF sequences found in 'QCAV-4' that resulted from the transgenic event.

DETAILED DESCRIPTION

The following detailed description of 'QCAV-4' is based on observations of plants that are approximately 25 months old. The 'QCAV-4' plants have been observed growing in a cultivated area in Lambells Lagoon, Northern Territory, Australia. Certain characteristics of this cultivar, such as growth and color, may change with changing environmental conditions (such as, light, temperature, moisture, nutrient availability, or other factors). Color descriptions and other terminology are used in accordance with their ordinary dictionary descriptions, unless the context clearly indicates otherwise.

BOTANICAL DESCRIPTION

Scientific name: *Musa acuminata* 'QCAV-4'

Parentage: Cavendish Grand Nain

Plant:

In the absence of significant disease pressure, 'QCAV-4' appears to be essentially phenotypically identical to the wild type parent 'Cavendish Grand Nain' (unpatented) (Table 1). This includes in relation to immature and mature plant characteristics, fruit characteristics, and yield.

TABLE 1

Comparison of 'QCAV-4' to parent 'Cavendish Grand Nain'*

| Organ/Plant Part: Context | 'QCAV-4' | 'Cavendish Grand Nain' |
|---|---|---|
| Ploidy: | triploid | triploid |
| Pseudostem: overlapping of leaf sheaths | weak | weak |
| Pseudostem: tapering | absent or weak | absent or weak |
| Pseudostem: colour | purple | purple |
| Pseudostem: anthocyanin colouration | medium to strong | medium |
| Pseudostem: colour of inner side of basal sheath | purple | purple |
| Plant: compactness of crown | compact | compact |
| Plant: growth habit | drooping | drooping |
| Petiole: attitude of wings at base | curved outwards | curved outwards |
| Leaf blade: colour of midrib on lower side | green | green |
| Leaf blade: shape of base | both sides acute | both sides acute |
| Leaf blade: waxiness on lower side | medium | weak to medium |
| Leaf blade: width | broad | broad |
| Leaf blade: glossiness of upper side | absent | absent |
| Peduncle: diameter | large | large |
| Peduncle: pubescence | present | present |
| Peduncle: curvature | medium to strong | medium to strong |
| Bunch: length | long | long |
| Bunch: shape | cylindrical | cylindrical |
| Bunch: attitude of fruits | moderately turned up | moderately turned up |
| Bunch: compactness | medium | medium |
| Bunch: number of hands | many | many |
| Rachis: attitude of male part | vertical | vertical |
| Rachis: prominence of scars | weak | weak |
| Rachis: persistence of bracts | absent or weak | absent or weak |
| Rachis: persistence of hermaphrodite flowers | present | present |
| Fruit: colour of peel (before maturity) | greenish yellow (RHS 141C) | greenish yellow (RHS 141C) |
| Fruit: persistence of floral organs | present | present |
| Male inflorescence: persistence | present | present |
| Male inflorescence: shape | narrow ovate | narrow ovate |
| Male inflorescence: opening of bracts | closed or slightly open | closed or slightly open |
| Bract: colour of inner side | orange red | orange red |
| Bract: shape of apex | broad acute | broad acute |

*For most characteristics, 4-5 individual plants were assessed.

However, a clear phenotype is observable under pressure from Fusarium wilt tropical race 4 (TR4).

In March 2018, an expanded field trial was planted which included 50 replicates of each of the four events from Trial 1, in 10×5 randomized plot design. In addition to recording disease incidence, detailed agronomic information such as bunch weight, number of fingers on the top hand and crop cycling time is also collected. Since the trial began, agronomic data for the plant crop and at least two ratoon crops were collected. The trial is ongoing. Based on the results of these field trials and molecular characterisation, 'QCAV-4' was selected.

The disease status of plants is assessed by the presence of characteristic disease symptoms (both external and internal) and by molecular testing of vascular tissue for the presence of the fungal pathogen TR4. The plants are inspected on a weekly basis and plants showing the characteristic external symptoms of the disease identified. About 1-2 weeks later, the pseudostem of these plants is cut and examined for the presence of the highly characteristic internal vascular discolouration associated with TR4 infection. DNA is extracted from the infected vascular tissue, and a highly sensitive PCR test is used to detect the presence of TR4, and this is confirmed by sequencing. The TR4 fungus from discoloured vascular tissue is obtained and DNA extracted and analysed using PCR to confirm the presence of TR4 (and also by sequencing).

As shown in Table 2, 'QCAV-4' can remain largely disease-free under the same conditions of TR4 pressure leading to greater than 80% infection rates in wild type 'Cavendish Grand Nain'.

TABLE 2

Resistance of Plants to *Fusarium* wilt tropical race 4 (TR4).

| Variety | Number of Plants | Number Infected | Percent Infected |
|---|---|---|---|
| 'Cavendish Grand Nain' | 50 | 32 | 64 |
| 'Cavendish Williams' (unpatented) | 50 | 38 | 76 |
| 'RGA2-5'(unpatented) | 50 | 14 | 28 |
| 'RGA2-2'(unpatented) | 50 | 8 | 16 |
| 'RGA2-3'(unpatented) | 50 | 3 | 6 |
| 'QCAV-4' | 50 | 0 | 0 |

TABLE 3

Fruit Production Characteristics

| | Plant crop | | | Ratoon 1 | | |
|---|---|---|---|---|---|---|
| Line | Bunch weight (kg) | No. of fingers (top hand) | Cycle 1 (days) | Bunch weight (kg) | No. of fingers (top hand) | Cycle 2 (days) |
| Grand Nain | 33.1 | 24.0 | 377.3 | 29.9 | 20.0 | 212.4 |
| Williams | 30.7 | 23.0 | 324.7 | 29.8 | 22.2 | 212.9 |
| RGA2-2 | 29.1 | 22.2 | 268.3 | 27.6 | 22.3 | 223.8 |
| RGA2-3 | 30.1 | 24.9 | 328.9 | 23.8 | 20.2 | 200.8 |
| _QCAV-4 | 28.1 | 22.5 | 331.1 | 24.3 | 19.7 | 199.2 |
| RGA2-5 | 35.5 | 24.8 | 341.6 | 30.6 | 22.0 | 212.9 |

| | Ratoon 2 | | |
|---|---|---|---|
| Line | Bunch weight (kg) | No. of fingers (top hand) | Cycle 3 (days) |
| Grand Nain | 31.7 | 26.5 | 206.6 |
| Williams | 40.4 | 25.9 | 211.8 |
| RGA2-2 | 28.1 | 24.1 | 215.5 |
| RGA2-3 | 29.2 | 26.1 | 211.7 |
| _QCAV-4 | 33.7 | 25.3 | 206.9 |
| RGA2-5 | 37.3 | 29.5 | 212.8 |

Height of about 180 to 250 cm—shorter than Giant Cavendish and taller than Dwarf Cavendish cultivars.

Moderate adult pseudostem width.

Relatively large bunch size.

Moderate fruit size.

Solid green leaf colour.

TABLE 4

Additional phenotypic details for 'QCAV-4'*

| Characteristic | QCAV-4 phenotype |
|---|---|
| Height of the pseudostem | 2 - (2.1 to 2.9 m). (mean value = 2.78 m for three plants). |
| Leaf habit/growth habit (upright, spreading, drooping) | 3 - Drooping. |
| Pseudostem diameter | 83.7 cm (mean value for 3 plants). |
| Attitude of petiole wings at base (curved outwards, straight, slightly curved inwards, moderately curved inwards, overlapping) | 1 - Open with margins spreading. |
| Petiole margins | 5 - Not winged and not clasping the pseudostem. |
| Petiole wing type | 1 - Dry. |
| Edge of petiole margin color | 1 - Colourless (without a colour line along) |
| Petiole length | 1 - ≤50 cm. Typically measured at 38 cm. |
| Blotches at the petiole base | 3 - Large blotches |
| Color designation of leaf blade midrib on lower side | Green (137C) |
| Leaf blade shape of base (both sides rounded, one side rounded and one side acute, both sides acute) | 1 - Both sides rounded. |
| Waxiness of lower side of leaf blade | 3 - Moderately waxy. |
| Leaf blade length | 3 - 221 to 260 cm. Typically measured at 222.7 cm. |
| Leaf blade width | 3 - 81 to 90 cm. Typically measured at 90 cm. |
| Leaf blade ratio length/width | 5 - 2.4 to 2.6. Typically measured at 2.5. |
| Appearance of leaf lower surface | 1 - Dull. |
| Color designation of midrib ventral surface | Green (137C) |
| Peduncle length, width, diameter | 2 - 31-60 cm<br>2 - 7-12 cm |
| Empty nodes on peduncle | 3-4 |
| Peduncle hairiness | 3 - Very hairy, short hairs (similar to velvet touch). |
| Bunch position | 1 - Hanging vertically. |
| Bunch shape (cylindrical, irregular, conical) | 1 - Cylindrical. |
| Bunch appearance | 1 - Lax (one can easily place one's hand between the hands of fruit). |
| Rachis type | 2 - Present and male bud may be degenerated or persistent. |
| Rachis position | 1 - Falling vertically. |
| Male bud type | 1 - Normal (present) |
| Male bud shape | 3 - Intermediate. |
| Bract base shape | 1 - Small shoulder. |
| Bract apex shape | 2 - Slightly pointed. |
| Color of the bract internal face | 169A. |
| Prominence of scars on the rachis (weak, strong) | 2 - Not prominent. |
| Fading of color on bract base | 1 - Color discontinuing towards the base (loss of pigmentation at the base). |
| Male bract shape | 3 - Ovate. |
| Typical width of bract | Approximately 12 cm |
| Typical length of bract | Approximately 28 cm |
| Male bract lifting | 3 - Lifting two or more at a time. |
| Bract behavior before falling | 1 - Revolute (rolling). |
| Wax on the bract | 3 - Moderately waxy. |
| Presence of grooves on the bract | 2 - Moderate grooving (parallel ridges are distinguishable). |

TABLE 4-continued

| Additional phenotypic details for 'QCAV-4'* | |
|---|---|
| Characteristic | QCAV-4 phenotype |
| Male flower behavior | 4 - Neutral/male flowers persistent. |
| Persistence of bracts on the rachis (absent or weak, strong) | 3 - Male flowers/bracts above the male bud (but the stalk is bare above flowers/bracts). |
| Shape of bract apex (narrow acute, broad acute, right angle, obtuse, emarginate) | 2 - Slightly pointed. |
| Fruit position | 3 - Curved upward (obliquely, at a 45° angle upward). |
| Fruit shape longitudinal curvature | 3 - Curved (sharp curve) |
| Fruit longitudinal ridges (absent or weak, moderate, strong) | 2 - Slightly ridged |
| Fruit shape of apex (rounded, truncate, bottle-necked, pointed) | 3 - Blunt-tipped |
| Fruit persistence of floral organs | 2 - Persistent style. |
| Adherence of the fruit peel | 1 - Fruit peels easily |
| Cracks in fruit peel | 1 - Without cracks |
| Fruit eating quality and main use | 1 - Dessert |

*phenotypic characteristics are presented using the descriptors set out in IPGRI, I. MAD. 1996. Descriptors for Banana. For most, observations from 3-6 individual plants.

TABLE 5

'QCAV-4' bunch characteristics*

| | BUNCH CHARACTERISTICS | | | |
|---|---|---|---|---|
| PLANT ID | LENGTH (cm) | DIA-METER (cm) | SHAPE | ATTITUDE OF FRUIT |
| 20221 | 88.3 | 122.6 | CONICAL | MODERATLY TURNED UP |
| 20223 | 72.0 | 123.0 | CONICAL | MODERATLY TURNED UP |
| 20229 | 83.0 | 127.0 | CONICAL | MODERATLY TURNED UP |
| 20231 | 75.0 | 113.0 | CONICAL | MODERATLY TURNED UP |
| 20241 | 72.0 | 120.0 | CONICAL | MODERATLY TURNED UP |
| 20242 | 77.5 | 110.0 | CONICAL | MODERATLY TURNED UP |
| 20247 | 76.0 | 132.0 | CONICAL | MODERATLY TURNED UP |
| 20248 | 82.0 | 142.0 | CONICAL | MODERATLY TURNED UP |
| 20251 | 88.0 | 122.5 | CONICAL | MODERATLY TURNED UP |
| 20255 | 59.0 | 118.0 | CONICAL | MODERATLY TURNED UP |
| 20257 | 88.5 | 122.3 | CONICAL | MODERATLY TURNED UP |
| 20263 | 83.0 | 128.0 | CONICAL | MODERATLY TURNED UP |
| 20268 | 80.0 | 146.0 | CONICAL | MODERATLY TURNED UP |
| 20269 | 88.5 | 126.0 | CONICAL | MODERATLY TURNED UP |
| 20273 | 84.0 | 120.0 | CONICAL | MODERATLY TURNED UP |

| | BUNCH CHARACTERISTICS | | | | | |
|---|---|---|---|---|---|---|
| PLANT ID | COM-PACT-NESS | # OF HANDS | Ripen-ing stage | CURVA-TURE | LONGI-TUDINAL RIDGES | LENGTH (cm) |
| 20221 | MEDIUM | 11 | 6 | EVENLY CURVED | MODER-ATE | 16.0 |

TABLE 5-continued

'QCAV-4' bunch characteristics*

| | | | | | | |
|---|---|---|---|---|---|---|
| 20223 | MEDIUM | 8 | 6 | EVENLY CURVED | MODER-ATE | 14.6 |
| 20229 | MEDIUM | 10 | 6 | EVENLY CURVED | MODER-ATE | 14.4 |
| 20231 | MEDIUM | 10 | 6 | EVENLY CURVED | MODER-ATE | 14.2 |
| 20241 | MEDIUM | | 6 | EVENLY CURVED | MODER-ATE | 13.6 |
| 20242 | MEDIUM | 10 | 6 | EVENLY CURVED | MODER-ATE | 14.0 |
| 20247 | MEDIUM | 10 | 6 | EVENLY CURVED | MODER-ATE | 13.8 |
| 20248 | MEDIUM | 10 | 6 | EVENLY CURVED | MODER-ATE | 15.4 |
| 20251 | MEDIUM | 11 | 6 | EVENLY CURVED | MODER-ATE | 15.4 |
| 20255 | MEDIUM | 8 | 6 | EVENLY CURVED | MODER-ATE | 13.7 |
| 20257 | MEDIUM | 10 | 6 | EVENLY CURVED | MODER-ATE | 14.5 |
| 20263 | MEDIUM | 10 | 6 | EVENLY CURVED | MODER-ATE | 13.8 |
| 20268 | MEDIUM | 9 | 6 | EVENLY CURVED | MODER-ATE | 15.5 |
| 20269 | MEDIUM | 11 | 6 | EVENLY CURVED | MODER-ATE | 14.0 |
| 20273 | MEDIUM | 11 | 6 | EVENLY CURVED | MODER-ATE | 13.0 |

*Observations from 15 individual plants. Bunch averages:_Length: 79.8 cm; Diameter: 124.8 cm; No. hands: 9.9

TABLE 6

'QCAV-4' fruit characteristics

| | FRUIT CHARACTERISTICS | | | | |
|---|---|---|---|---|---|
| PLANT ID | FRUIT WIDTH (cm) | LENGTH OF PEDICEL (cm) | SHAPE OF APEX | THICK-NESS OF PEEL (mm) | COLOUR OF PEEL (RH52015) |
| 20221 | 3.5 | 2.8 | TRUNCATE | 3.8 | Light Greenish Yellow 3B-3D and 4B |
| 20223 | 3.2 | 3.4 | TRUNCATE | 4.1 | Light Greenish Yellow 3B-3D and 4B |
| 20229 | 3.4 | 2.9 | TRUNCATE | 3.2 | Light Greenish Yellow 3B-3D and 4B |
| 20231 | 3.4 | 3.0 | TRUNCATE | 3.2 | Light Greenish Yellow 3B-3D and 4B |
| 20241 | 3.4 | 3.2 | TRUNCATE | 3.3 | Light Greenish Yellow 3B-3D and 4B |
| 20242 | 3.5 | 2.6 | TRUNCATE | 3.0 | Light Greenish Yellow 3B-3D and 4B |
| 20247 | 3.3 | 3.4 | TRUNCATE | 3.5 | Light Greenish Yellow 3B-3D and 4B |

TABLE 6-continued

| 'QCAV-4' fruit characteristics | | | | | |
|---|---|---|---|---|---|
| 20248 | 3.9 | 3.3 | TRUNCATE | 3.5 | Light Greenish Yellow 3B-3D and 4B |
| 20251 | 3.3 | 3.3 | TRUNCATE | 3.7 | Light Greenish Yellow 3B-3D and 4B |
| 20255 | 3.4 | 2.2 | TRUNCATE | 3.2 | Light Greenish Yellow 3B-3D and 4B |
| 20257 | 3.6 | 2.5 | TRUNCATE | 4.0 | Light Greenish Yellow 3B-3D and 4B |
| 20263 | 3.3 | 3.2 | TRUNCATE | 4.5 | Light Greenish Yellow 3B-3D and 4B |
| | 3.7 | 3.2 | TRUNCATE | 3.1 | Light 20268 Yellow 3B-3D and 4B |
| 20269 | 3.4 | 3.8 | TRUNCATE | 3.2 | Light Greenish Yellow 3B-3D and 4B |
| 20273 | 2.8 | 3.1 | TRUNCATE | 2.7 | Light Greenish Yellow 3B-3D and 4B |

| | FRUIT CHARACTERISTICS | | | |
|---|---|---|---|---|
| PLANT ID | ADHERENCE OF PEEL | COLOUR OF FLESH | FIRMNESS OF FLESH | PRESENCE OF SEED |
| 20221 | PEELS EASILY | CREAM | MEDIUM | ABSENT |
| 20223 | PEELS EASILY | CREAM | MEDIUM | ABSENT |
| 20229 | PEELS EASILY | CREAM | MEDIUM | ABSENT |
| 20231 | PEELS EASILY | CREAM | MEDIUM | ABSENT |
| 20241 | PEELS EASILY | CREAM | MEDIUM | ABSENT |
| 20242 | PEELS EASILY | CREAM | MEDIUM | ABSENT |
| 20247 | PEELS EASILY | CREAM | MEDIUM | ABSENT |
| 20248 | PEELS EASILY | CREAM | MEDIUM | ABSENT |
| 20251 | PEELS EASILY | CREAM | MEDIUM | ABSENT |
| 20255 | PEELS EASILY | CREAM | MEDIUM | ABSENT |
| 20257 | PEELS EASILY | CREAM | MEDIUM | ABSENT |
| 20263 | PEELS EASILY | CREAM | MEDIUM | ABSENT |
| | PEELS EASILY | CREAM | MEDIUM | ABSENT |
| 20269 | PEELS EASILY | CREAM | MEDIUM | ABSENT |
| 20273 | PEELS EASILY | CREAM | MEDIUM | ABSENT |

*Observations from 15 individual plants. Fruit averages: _Length: 14.4 cm; Width: 3.4 cm; Peel thickness: 0.35 cm

TABLE 7

Average cycle time in days per cycle for 'QCAV-4' healthy plants only*

| | Cycle time days | | | | |
|---|---|---|---|---|---|
| | Plant | R1 | R2 | R3 | R4 |
| 'RGA2-2' | 339.5 | 223.8 | 208.1 | 216 | 219.4 |
| 'RGA2-3' | 329 | 200.8 | 210.7 | 201.5 | 187 |
| 'QCAV-4' | 331.1 | 199.2 | 210.8 | 174.9 | 189.8 |
| 'RGA2-5' | 341.6 | 212.9 | 208.6 | 205.4 | 207.1 |
| 'Grand Nain' | 327.3 | 211.7 | 206.4 | 206.2 | 213.5 |
| 'Williams' | 324.7 | 212.3 | 219.3 | 206.3 | 232 |

*Observations from 50 individual plants for each variety.

TABLE 8

Average yield in kg per cycle for 'QCAV-4' healthy plants only*

| | Average yield Kg | | | | |
|---|---|---|---|---|---|
| | Plant | R1 | R2 | R3 | R4 |
| 'RGA2-2' | 29.1 | 27.6 | 28 | 31.1 | 36.4 |
| 'RGA2-3' | 30 | 23.8 | 27.8 | 25.4 | 31.9 |
| 'QCAV-4' | 28.1 | 24.3 | 31.7 | 28.5 | 34.8 |
| 'RGA2-5' | 35.5 | 30.6 | 32.3 | 32 | 35.8 |
| 'Grand Nain' | 33.1 | 29.6 | 32.1 | 29.8 | 35.7 |
| 'Williams' | 30.7 | 30.1 | 35.1 | 33.7 | 37.4 |

*Observations from 50 individual plants for each variety.

TABLE 9

Comparative TR4 resistance*
Cumulative new infections per cycle (%)

| | Plant | R1 | R2 | R3 | R4 |
|---|---|---|---|---|---|
| 'RGA2-2' | 2 | 2 | 2 | 8 | 20 |
| 'RGA2-3' | 2 | 2 | 2 | 2 | 6 |
| 'QCAV-4 | 0 | 0 | 0 | 0 | 2 |
| 'RGA2-5' | 2 | 6 | 10 | 16 | 36 |
| 'Grand Nain' | 6 | 26 | 40 | 54 | 66 |
| 'Williams' | 2 | 14 | 22 | 38 | 84 |

*Observations from 50 individual plants for each variety.

Southern Analysis:

Genomic DNA was extracted from 'QCAV-4' and wild type (non-transformed) Cavendish Grand Nain. The DNA was digested with a restriction enzyme, electrophoresed through an agarose gel, transferred to a membrane, and probed with a labelled RGA2 probe.

As shown in FIG. 1A, Southern analysis was consistent with four transgene copies in 'QCAV-4', in addition to the endogenous RGA2 genes. Cavendish Grand Nain is a triploid and it could be expected to have three endogenous copies of RGA2. Two distinct bands were identified in the wild type, indicating that two of three endogenous copies may have migrated together.

Figure 1B:
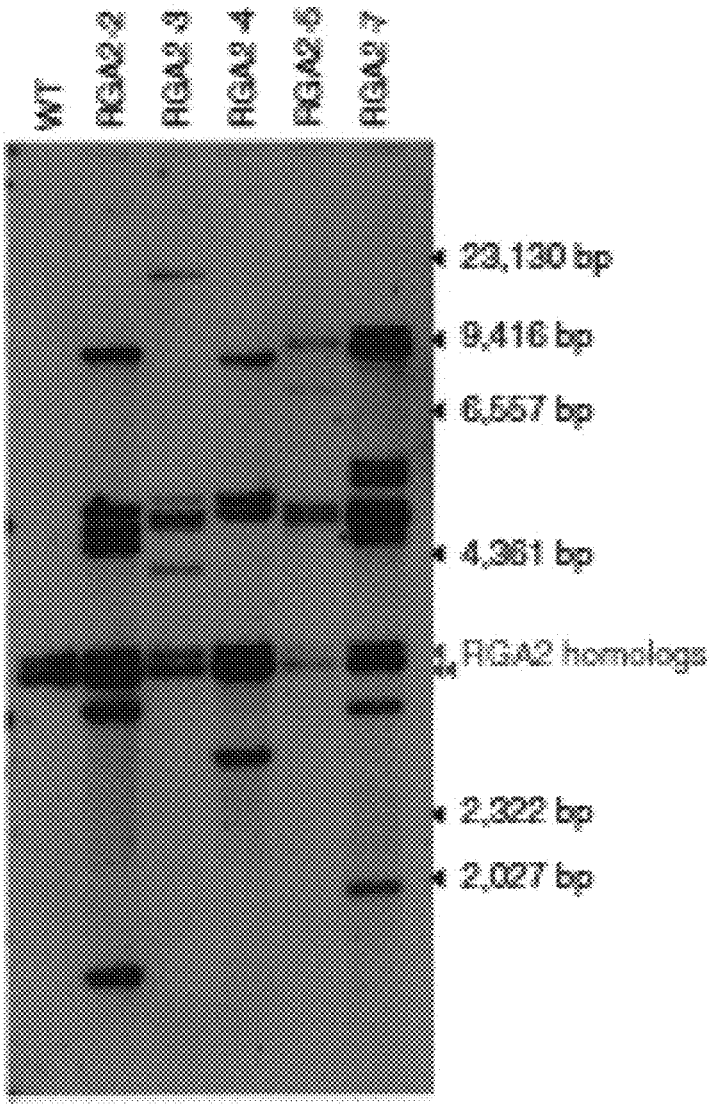
FIG. 1B is a digital image of Southern blot analysis of wild type Cavendish Grand Nain (parent) and independent transgenic lines 'RGA2-2', 'RGA2-3', 'RGA2-4' (clonal progenitor of 'QCAV-4'), 'RGA2-5' and 'RGA2-7' showing distinct pattern of transgenic RGA2 insertions, in addition to the three endogenous RGA2 copies.

Similar experiments were performed with wild type Cavendish Grand Nain (parent) and independent transgenic lines 'RGA2-2', 'RGA2-3', 'RGA2-4' (clonal progenitor of 'QCAV-4'), 'RGA2-5' and 'RGA2-7'. As shown in FIG. 1B, each line has a distinct pattern of transgenic RGA2 insertions, in addition to the three endogenous RGA2 copies.

Genome sequencing:

Long Read Sequencing of Event 'QCAV-4'

High molecular weight genomic DNA (with average fragment size >50 Kb) was isolated from young in vitro leaf tissue of 'QCAV-4' using GenElute Plant Genomic DNA Miniprep Kit (Sigma-Aldrich, USA). For long-read sequencing on PacBio Sequel II platform (Novogene, China), a size-selected library with an insert size of 20 Kb was generated. A total of ~75 Gbp data was obtained in CLR mode (4.9 M reads with a read length N50 of 17,973 bp). This corresponds to ~42× coverage of the Cavendish genome at the haplotype level. SAN-3 binary vector T-DNA sequence was used to filter out long-reads from the total genomic pool. About 80 long-reads which mapped onto the T-DNA sequence were then assembled using Flye plugin in Geneious Prime 2020. A single ~27 kb T-DNA insertion locus was assembled. This sequence, along with 5 kb flanking sequence, was polished using 'RGA2-4' genomic Illumina short reads (previously generated using Novaseq 6000) to correct a few Flye assembly errors (short indels). Nucleotide BLAST using the two flanking sequences of this T-DNA locus revealed that the insertion of T-DNA locus has occurred in chromosome 6 of the banana genome.

Details of the T-DNA Insertion

Event 'QCAV-4' contains a complex T-DNAs insert of 26,849 bp at a single genomic location on chromosome 6 between position 29,939,311 and 29,939,427 (−strand) creating a 116 bp deletion. The insert is located in an intergenic region between two intact predicted genes: Ma06_t28200.1 (a putative Malectin_like domain-containing protein) at position chr06:29,931,700..29,937,001 (+strand) and Ma06_t28210.1 (a malectin_like domain-containing protein) at position chr06:29,944,119..29,947,729 (+strand). Both genes are not affected by the insertion and it is not predicted that the insertion will affect their expression.

Figure 2A:
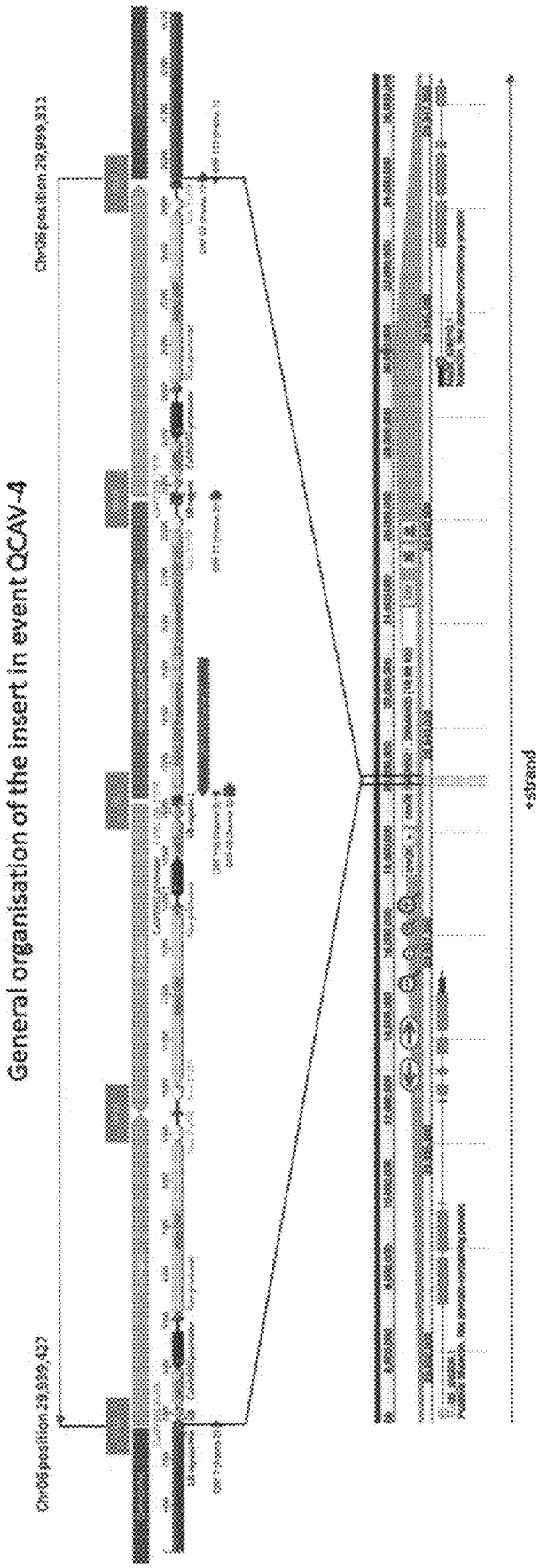
FIG. 2A is a schematic diagram showing the general organization of the insert in event 'QCAV-4'.
Figure 2B:
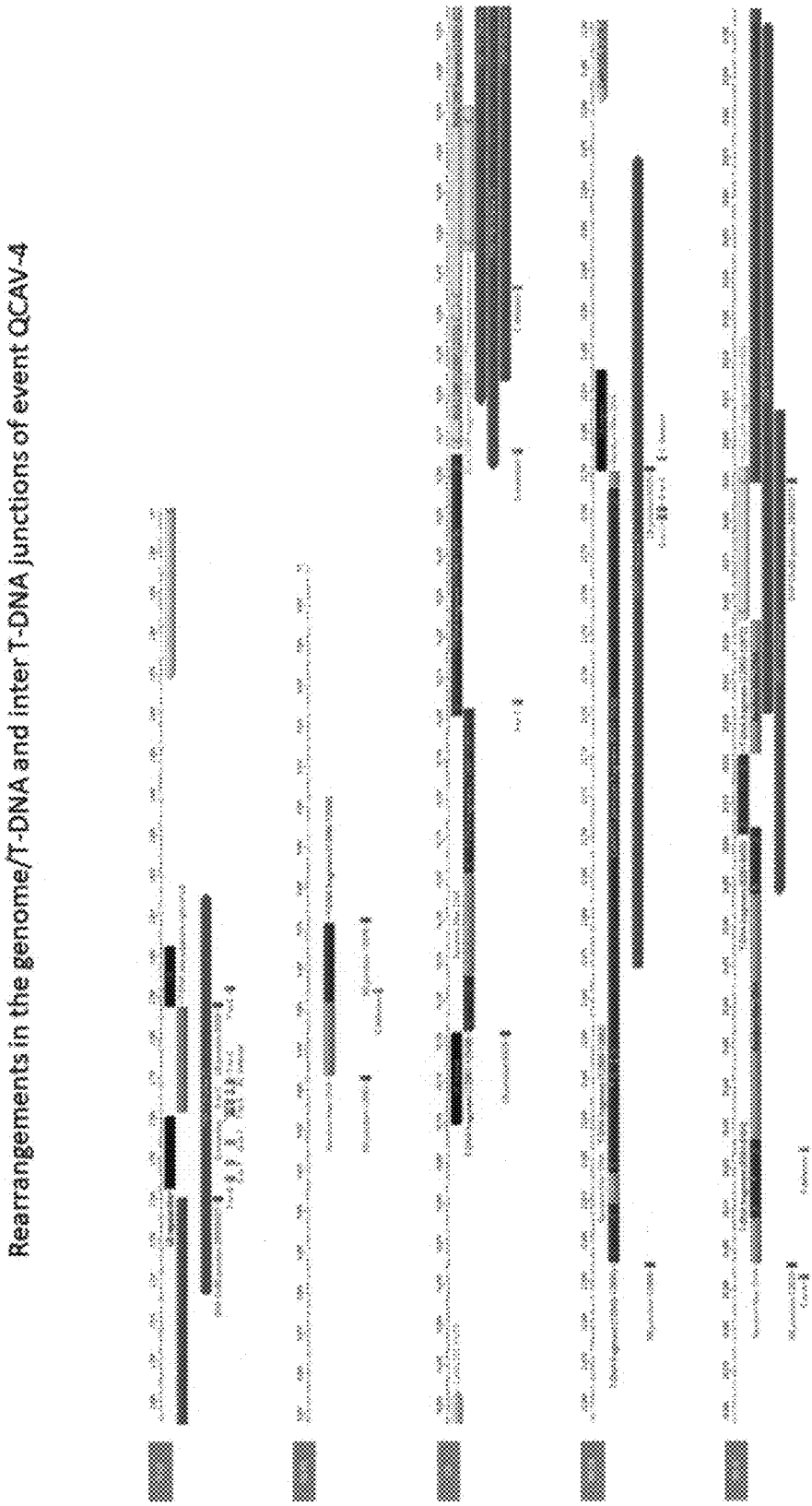
FIG. 2B is a schematic diagram showing the rearrangements in the genome/T-DNA and inter T-DNA junctions of event 'QCAV-4', demonstrating seven (7) new ORFs have been identified in the inter T-DNA regions of the transgenic insert of 'QCAV-4'.
Figure 2C:
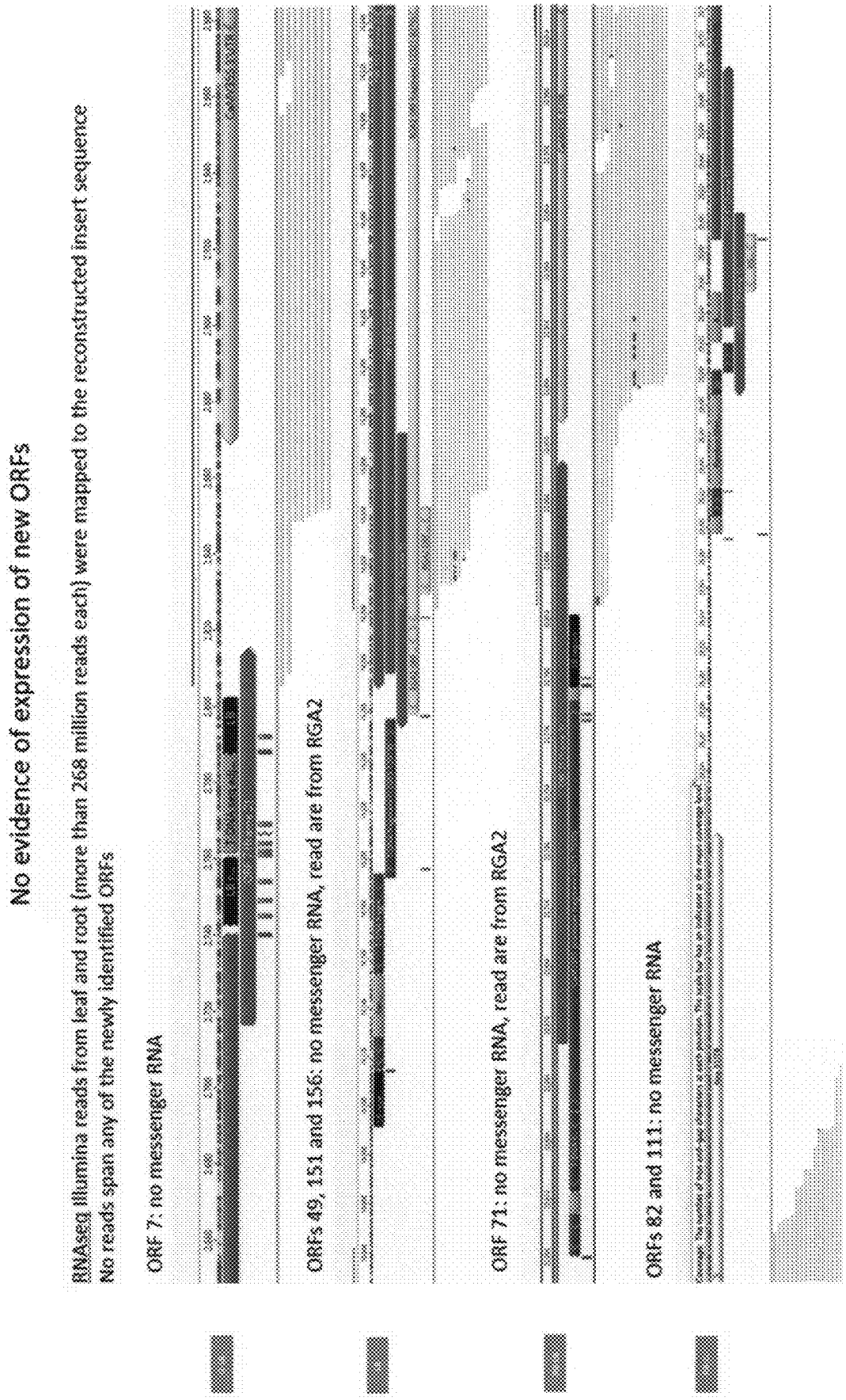
FIG. 2C is a schematic diagram showing that there is no evidence of expression of the seven new open reading frames (ORFs) in 'QCAV-4'.
Figure 3:
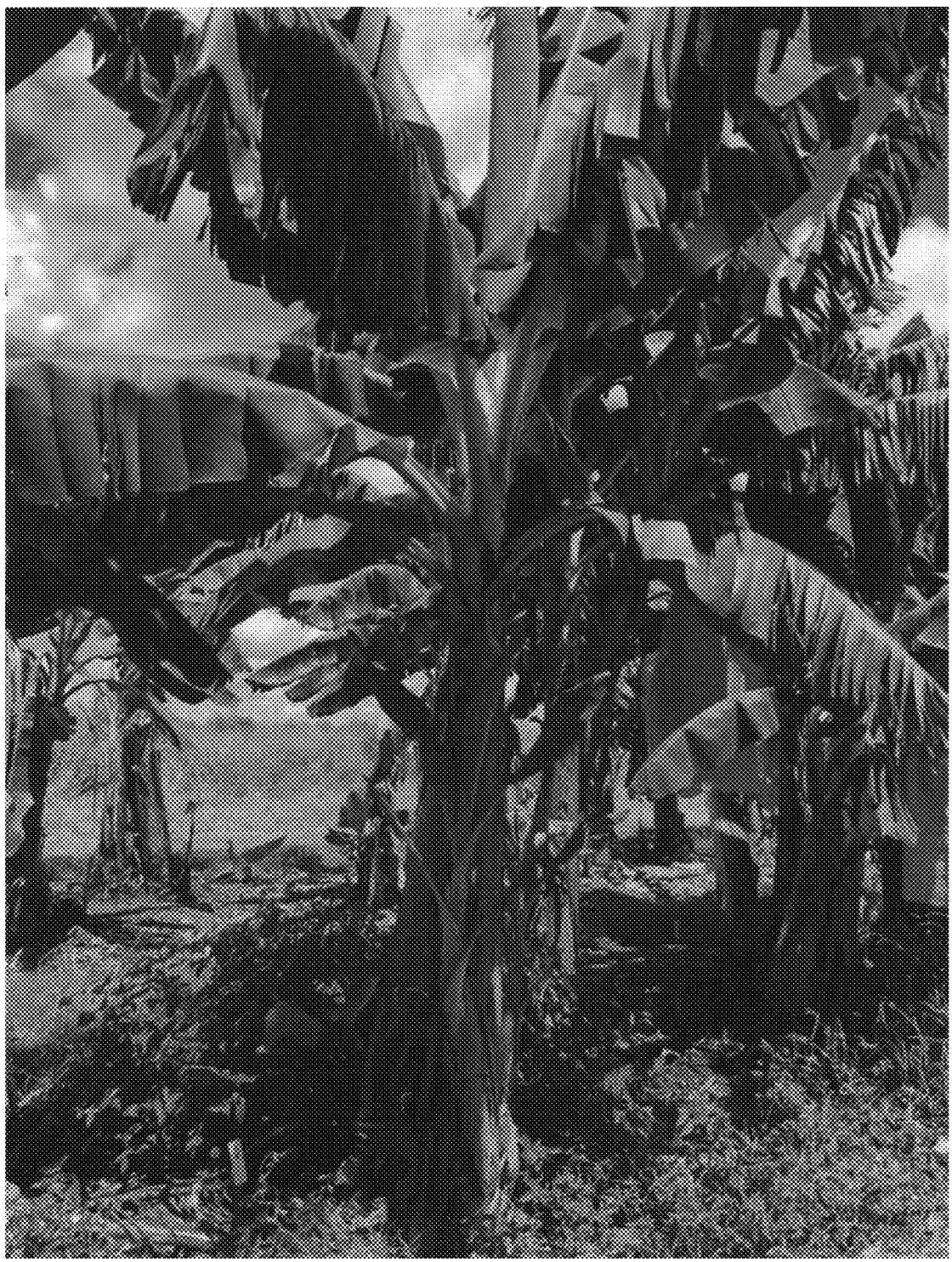
FIGS. 3-4 are photographs showing 'QCAV-4' at adult stage.
Figure 4:
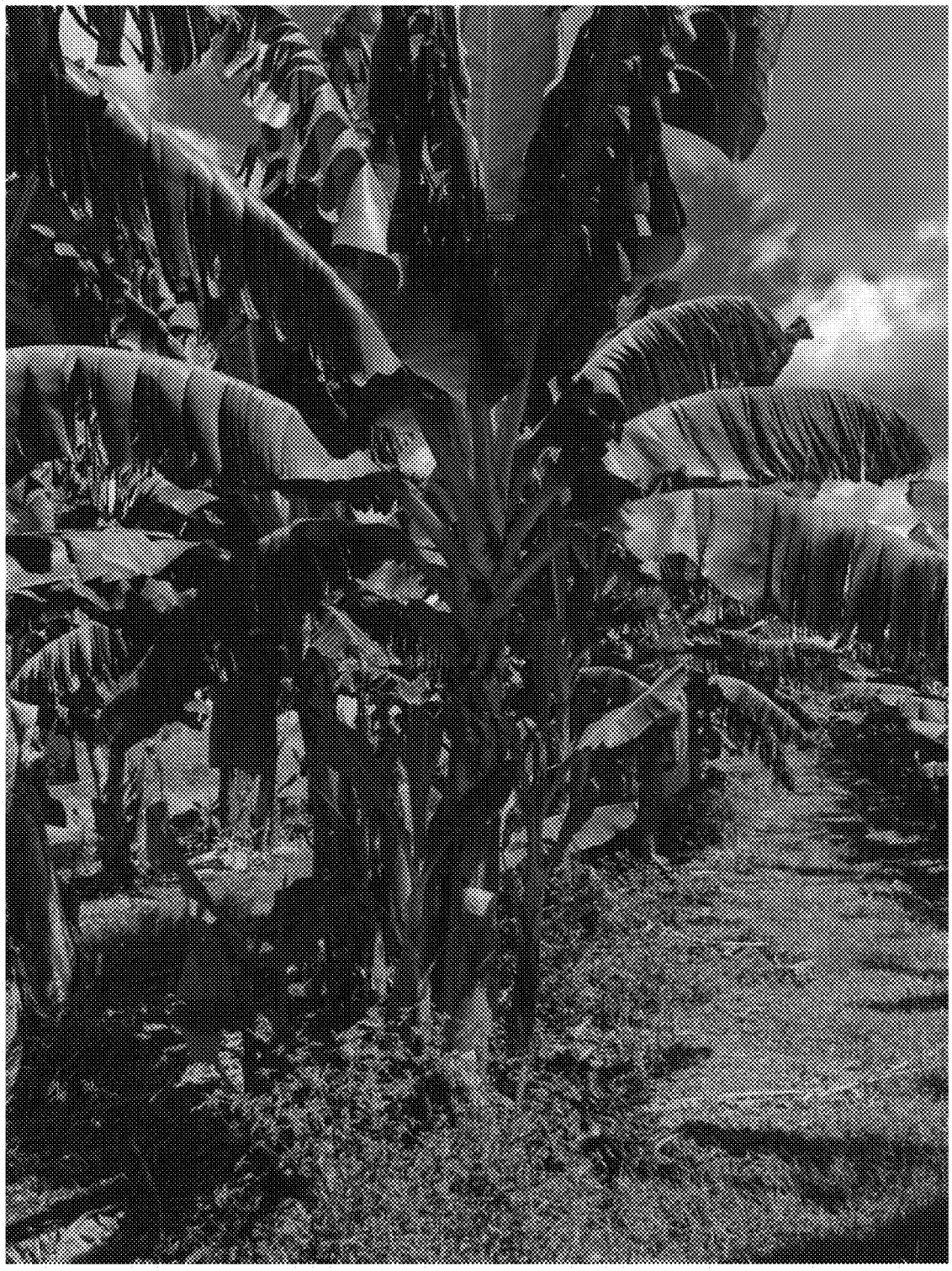
Figure 5:
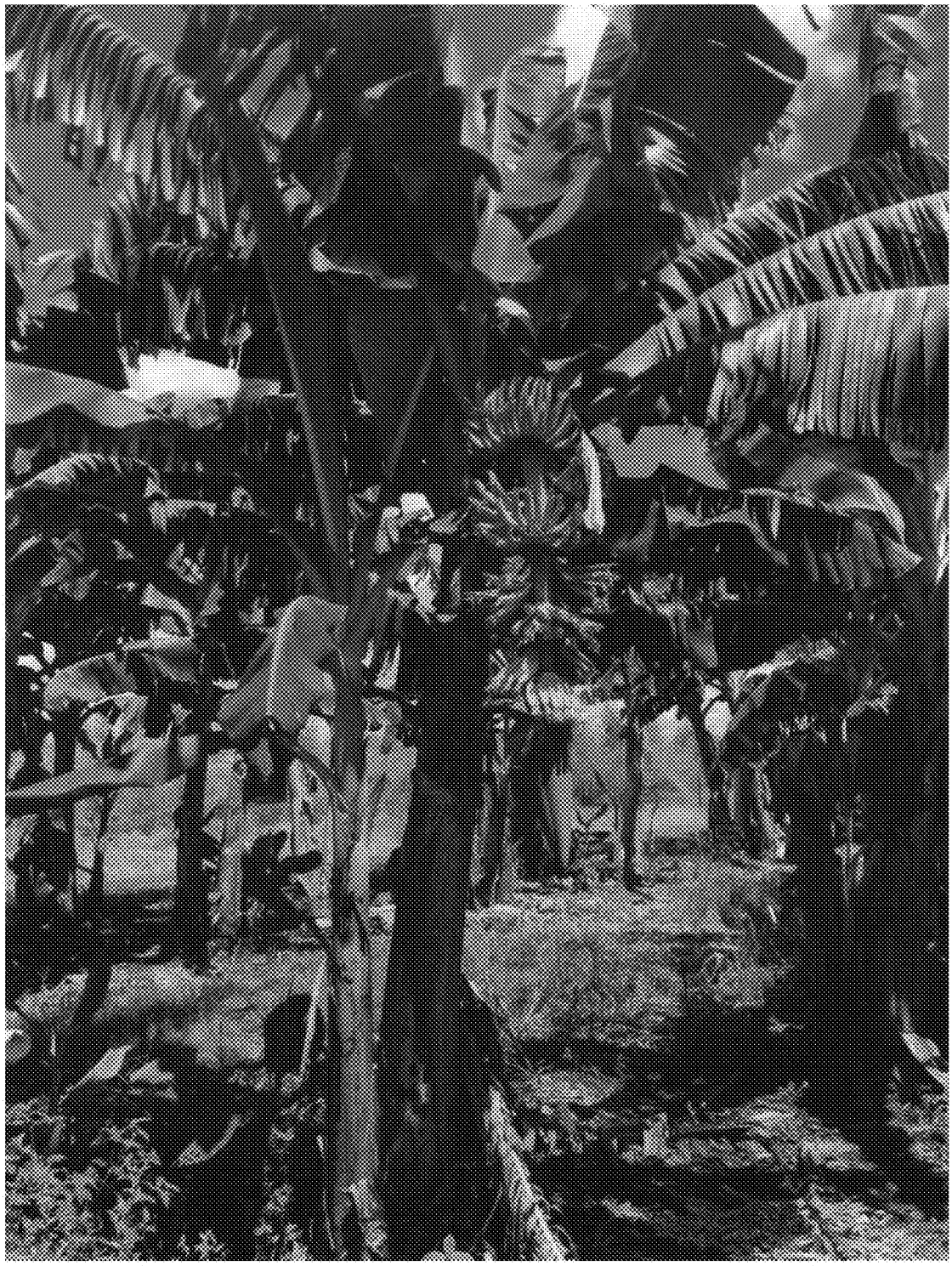
FIG. 5 is photograph showing 'QCAV-4' at adult stage and developing fruit.
Figure 6:
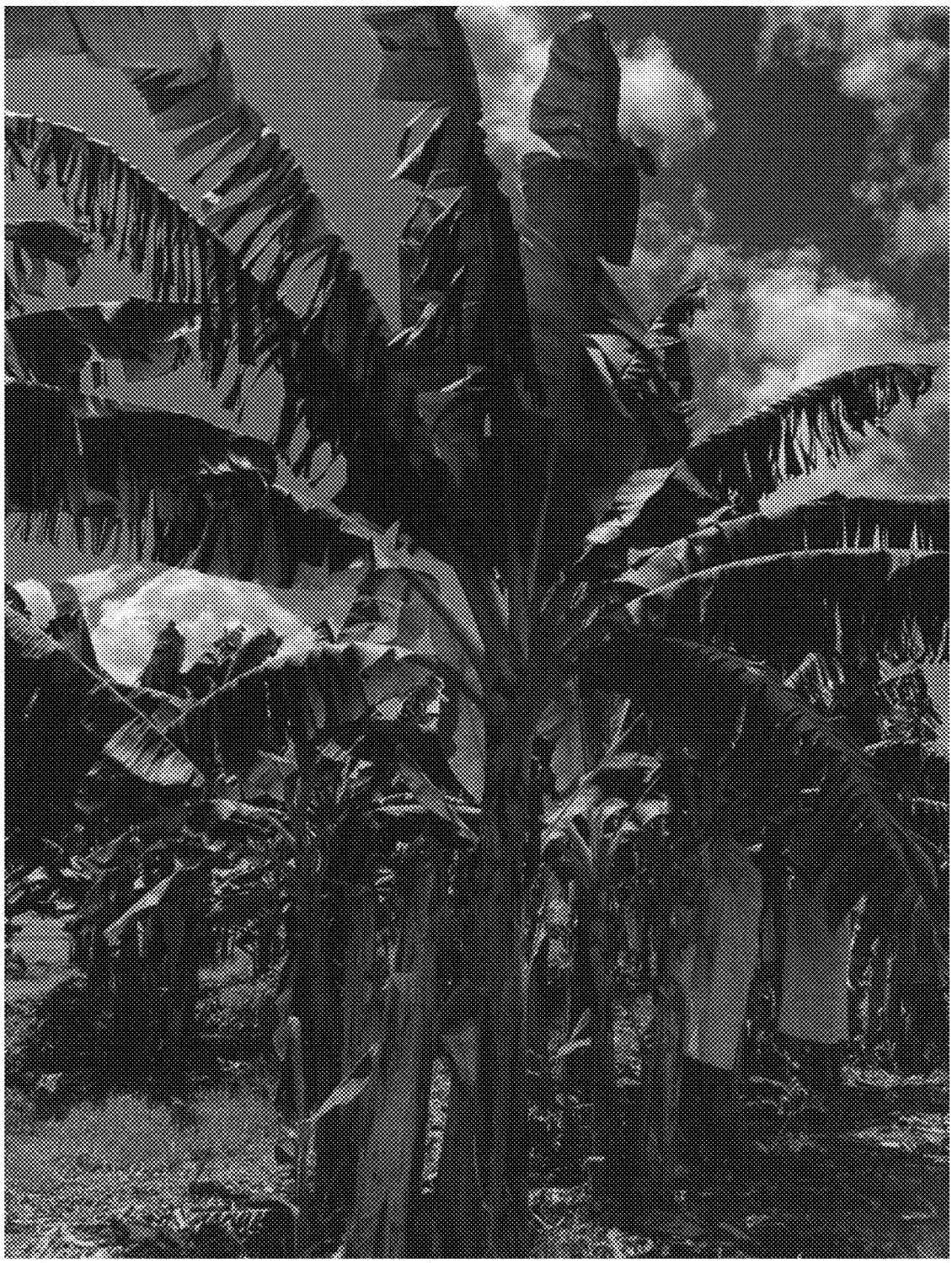
FIGS. 6-7 are photographs showing 'QCAV-4' at adult stage.
Figure 7:
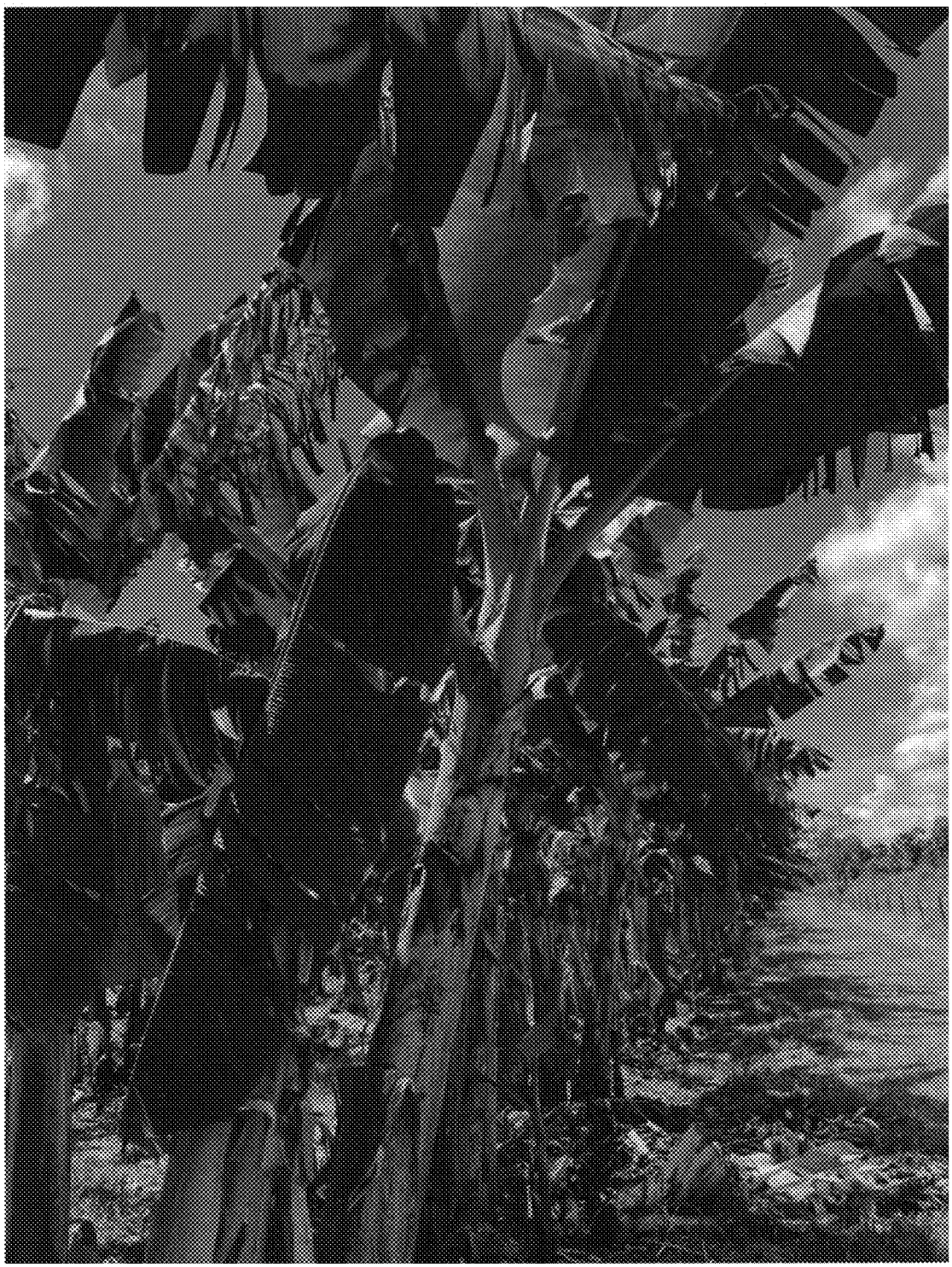
Figure 8:
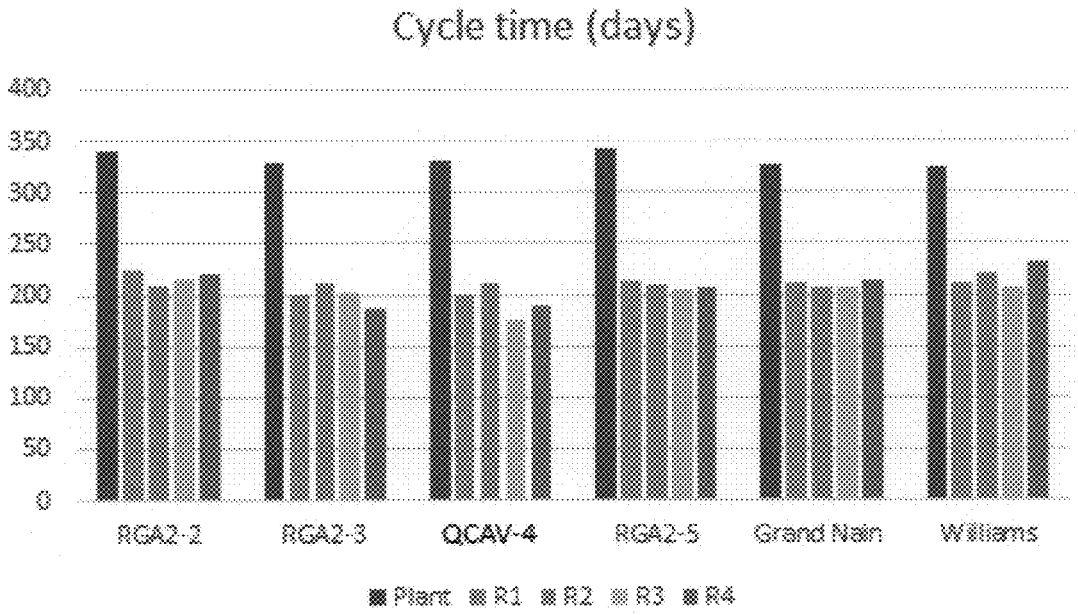
FIGS. 8-9 are graphical representations of the data shown in Tables 7-8, respectively.
Figure 9:
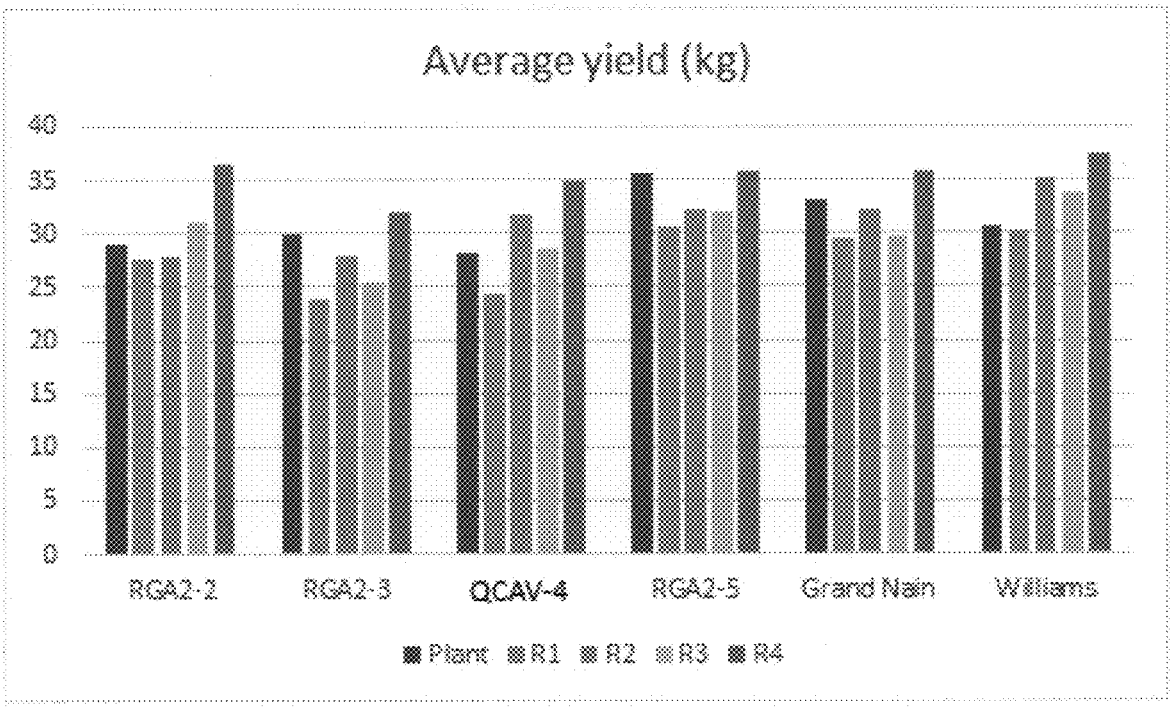
Figure 10:
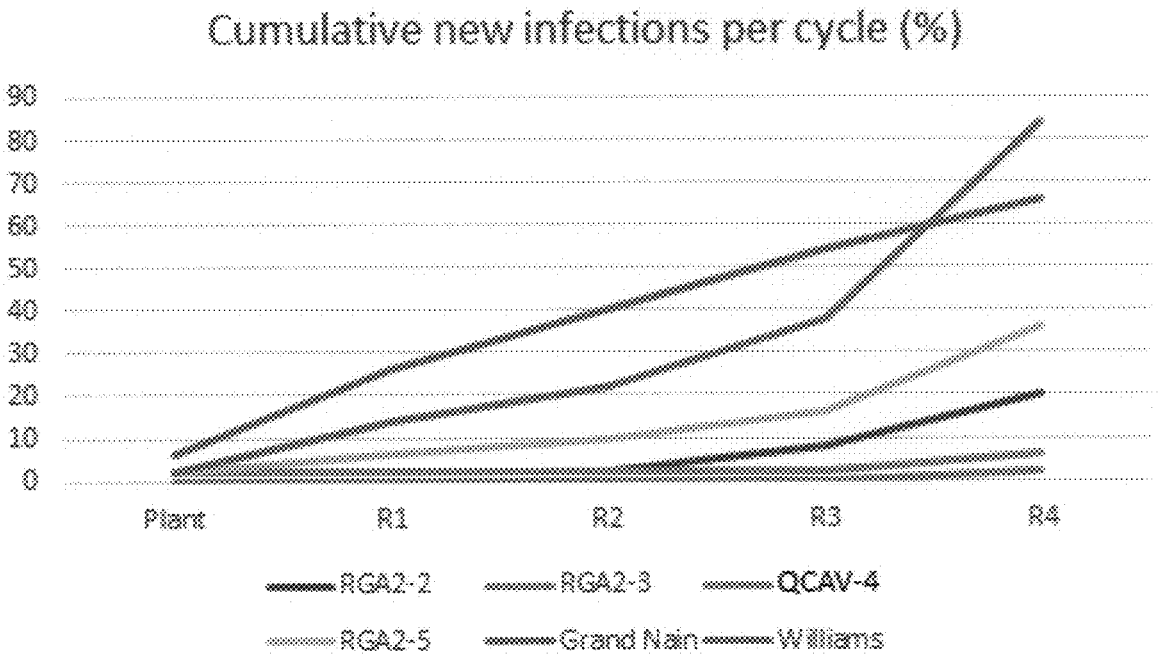
FIG. 10 is a graphical representation of the data shown in Table 9.

The insert itself is composed of three full and functional copies of the 6702 bp T-DNA (T-DNA 1 to 3, see FIGS. 2A-2C). In addition, two fragmented portions of the 'RGA2' ORF have recombined in opposite directions and inserted between T-DNA2 and T-DNA3. There are two genome/T-DNA and 3 inter T-DNA junctions with various levels of rearrangement (FIGS. 2A-2C).

New Open Reading Frames (ORFs) Analysis

The analysis identified 7 new ORFs (SEQ ID NOS: 1-7), all originating from these rearranged genome/T-DNA and inter T-DNA junctions. New ORFs AA sequences as follows:

```
>ORF_151_(frame_2)
                                        (SEQ ID NO: 1)
MWVCVSDDFDVKRITREITEYATNGRFMDLTNLNMLQVNLKEEIRGTTFL

LVLDDVWNEDPVKWESLLAPLDAGGRGSVVIVTTQSKKVADVTGTMEPYV

LEELTEDDSWSLIESHSFREASCSSTNPRMEEIGRKIAKKISGLPYGATA

MGRYLRSKHGESSWREVLETETWEMPPAASDVLSALRRSYDNLPPQLKLC

FAFCALFTKGYRFRKDTLIHMWIAQNLIQSTESKRSEDMAEECFDDLVCR

FFFRYSWGNYVMNDSVHDLARWVSLDEYFRADEDSPLHISKPIRHLSWCS

ERITNVLEDNNTGGDAVNPLSSLRTLLFLGQSEFRSYHLLDRMFRMLSRI

RVLDFSNCVIRNLPSSVGNLKHLRYLGLSNTRIQRLPESVTRLCLLQTLL

LEGCELCRLPRSMSRLVKLRQLKANPDVIADIAKVGRLIELQELKAYNVD
```

-continued

```
KKKGHGIAELSAMNQLHGDLSIRNLQNVEKTRESRKARLDEKQKLKLLDL

RWADGRGAGECDRDRKVLKGLRPHPNLRELSIKYYGGTSSPSWMTDQYLP

NMETIRLRSCARLTELPCLGQLHILRHLHIDGMSQVRQINLQFYGTGEVS

GFPLLELLNIRRMPSLEEWSEPRRNCCYFPRLHKLLIEDCPRLRNLPSLP

PTLEELRISRTGLVDLPGFHGNGDVTTNVSLSSLHVSECRELRSLSEGLL

QHNLVALKTAAFTDCDSLEFLPAEGFRTAISLESLIMTNCPLPCSFLLPS

SLEHLKLQPCLYPNNNEDSLSTCFENLTSLSFLDIKDCPNLSSFPPGPLC

QLSALQHLSLVNCQRLQSIGFQALTSLESLTIQNCPRLTMSHSLVEVNNS

SDTGLAFNITRWMRRRTGDDGLMLRHRAQNDSFFGGLLQHLTFLQFLKIC

QCPQLVTFTGEEEEKWRNLTSLQILHIVDCPNLEVLPANLQSLCSLSTLY

IVRCPRIHAFPPGGVSMSLAHLVIHECPQLCQHVPGTFGHP*

>ORF_156_(frame_3)
                                        (SEQ ID NO: 2)
MRFLPEVSACPWHIWSSMNALSCVSMSLAHLVIHECPQP*

>ORF_111_(frame_1)
                                        (SEQ ID NO: 3)
MHVMLYSWIRRGREDDSGGSIRITHYYGQFKLKAGANSH*

>ORF_87_(frame_1)
                                        (SEQ ID NO: 4)
MCYSDRSSRVVFPAPPNPTIEHHMHSGIIENKNLKFSTEKCFVIVRRLVH

KTENVK*

>ORF_71_(frame_3)
                                        (SEQ ID NO: 5)
MPLPTVVPKMDPHPRGASWKKKTFQPRLQSKWIDVNMLEQLWRIYCGVNK

LTLRQLNNTLRTFLMY*

>ORF_49_(frame_3)
                                        (SEQ ID NO: 6)
MTKCARDMLTQLRAFMDDQMCQGHADTSGRKRMDSWASDDVQGAEGAEAL

QVCRQYLQVWTINDVQNLKRSKVSPLLFLFAGEGYELWTLADL*

>ORF_7_(frame_2)
                                        (SEQ ID NO: 7)
MDRHLKSRIRFWFKQQWPRQLNNTLRCKQIDA*
```

Assessment of the Expression of the Seven New ORFs

To assess the expression potential of the seven newly identified ORFs, two RNAseq Illumina libraries were used. Root and leaf RNAseq libraries containing 274,556,348 and 268,119,840 reads, respectively were mapped to the reconstructed insertion locus. From this analysis, 1,029,853 and 781,191 reads originating from the leaf and root RNAseq dataset respectively mapped to the insert sequence. No read from either library mapped continuously across any of the seven newly identified ORFs, confirming the lack of mRNA originating from them in event QCAV-4.

Bioinformatic Assessment of the Allergenicity Potential the Seven New ORFs

In silico analyses performed (see below) to compare amino acid sequence of each new ORF to known allergenic proteins in the Food Allergy Research and Resource Program (FARRP) dataset, which is available through AllergenOnline (University of Nebraska). Full length sequence (E value $<10^{-5}$), 80-mer sliding window (35% homology with E value $<10^{-4}$) and 8-mer exact match searches identified no sequences similarity between any of the 7 new ORFs and known allergens in the database.

Bioinformatic Assessment of the Toxicity Potential of the Seven New ORFs

Potential structural similarities shared between the seven new ORFs and sequences in a protein toxin database were evaluated using the Basic Local Alignment Search Tool (BLAST) available within the Geneious program.

A blastp search using the BLOSUM45 similarity scoring matrix and the amino acid sequence from the seven new ORFs as the query sequence did not return any accessions of biological significance from the toxin database with an E-score acceptance criteria lower than $1\times10^{-4}$.

SEQUENCE LISTING

```
<160> NUMBER OF SEQ ID NOS: 7

<210> SEQ ID NO 1
<211> LENGTH: 991
<212> TYPE: PRT
<213> ORGANISM: Artificial Sequence
<220> FEATURE:
<223> OTHER INFORMATION: ORF 151

<400> SEQUENCE: 1

Met Trp Val Cys Val Ser Asp Asp Phe Asp Val Lys Arg Ile Thr Arg
1               5                   10                  15

Glu Ile Thr Glu Tyr Ala Thr Asn Gly Arg Phe Met Asp Leu Thr Asn
            20                  25                  30

Leu Asn Met Leu Gln Val Asn Leu Lys Glu Glu Ile Arg Gly Thr Thr
        35                  40                  45

Phe Leu Leu Val Leu Asp Asp Val Trp Asn Glu Asp Pro Val Lys Trp
    50                  55                  60

Glu Ser Leu Leu Ala Pro Leu Asp Ala Gly Gly Arg Gly Ser Val Val
65                  70                  75                  80

Ile Val Thr Thr Gln Ser Lys Lys Val Ala Asp Val Thr Gly Thr Met
                85                  90                  95

Glu Pro Tyr Val Leu Glu Glu Leu Thr Glu Asp Asp Ser Trp Ser Leu
            100                 105                 110

Ile Glu Ser His Ser Phe Arg Glu Ala Ser Cys Ser Ser Thr Asn Pro
        115                 120                 125

Arg Met Glu Glu Ile Gly Arg Lys Ile Ala Lys Lys Ile Ser Gly Leu
    130                 135                 140

Pro Tyr Gly Ala Thr Ala Met Gly Arg Tyr Leu Arg Ser Lys His Gly
145                 150                 155                 160

Glu Ser Ser Trp Arg Glu Val Leu Glu Thr Glu Thr Trp Glu Met Pro
                165                 170                 175

Pro Ala Ala Ser Asp Val Leu Ser Ala Leu Arg Arg Ser Tyr Asp Asn
            180                 185                 190

Leu Pro Pro Gln Leu Lys Leu Cys Phe Ala Phe Cys Ala Leu Phe Thr
        195                 200                 205

Lys Gly Tyr Arg Phe Arg Lys Asp Thr Leu Ile His Met Trp Ile Ala
    210                 215                 220

Gln Asn Leu Ile Gln Ser Thr Glu Ser Lys Arg Ser Glu Asp Met Ala
225                 230                 235                 240

Glu Glu Cys Phe Asp Asp Leu Val Cys Arg Phe Phe Phe Arg Tyr Ser
                245                 250                 255

Trp Gly Asn Tyr Val Met Asn Asp Ser Val His Asp Leu Ala Arg Trp
            260                 265                 270

Val Ser Leu Asp Glu Tyr Phe Arg Ala Asp Glu Asp Ser Pro Leu His
        275                 280                 285

Ile Ser Lys Pro Ile Arg His Leu Ser Trp Cys Ser Glu Arg Ile Thr
    290                 295                 300
```

-continued

```
Asn Val Leu Glu Asp Asn Asn Thr Gly Gly Asp Ala Val Asn Pro Leu
305                 310                 315                 320

Ser Ser Leu Arg Thr Leu Leu Phe Leu Gly Gln Ser Glu Phe Arg Ser
                325                 330                 335

Tyr His Leu Leu Asp Arg Met Phe Arg Met Leu Ser Arg Ile Arg Val
            340                 345                 350

Leu Asp Phe Ser Asn Cys Val Ile Arg Asn Leu Pro Ser Ser Val Gly
        355                 360                 365

Asn Leu Lys His Leu Arg Tyr Leu Gly Leu Ser Asn Thr Arg Ile Gln
    370                 375                 380

Arg Leu Pro Glu Ser Val Thr Arg Leu Cys Leu Leu Gln Thr Leu Leu
385                 390                 395                 400

Leu Glu Gly Cys Glu Leu Cys Arg Leu Pro Arg Ser Met Ser Arg Leu
                405                 410                 415

Val Lys Leu Arg Gln Leu Lys Ala Asn Pro Asp Val Ile Ala Asp Ile
            420                 425                 430

Ala Lys Val Gly Arg Leu Ile Glu Leu Gln Glu Leu Lys Ala Tyr Asn
        435                 440                 445

Val Asp Lys Lys Lys Gly His Gly Ile Ala Glu Leu Ser Ala Met Asn
    450                 455                 460

Gln Leu His Gly Asp Leu Ser Ile Arg Asn Leu Gln Asn Val Glu Lys
465                 470                 475                 480

Thr Arg Glu Ser Arg Lys Ala Arg Leu Asp Glu Lys Gln Lys Leu Lys
                485                 490                 495

Leu Leu Asp Leu Arg Trp Ala Asp Gly Arg Gly Ala Gly Glu Cys Asp
            500                 505                 510

Arg Asp Arg Lys Val Leu Lys Gly Leu Arg Pro His Pro Asn Leu Arg
        515                 520                 525

Glu Leu Ser Ile Lys Tyr Tyr Gly Gly Thr Ser Ser Pro Ser Trp Met
    530                 535                 540

Thr Asp Gln Tyr Leu Pro Asn Met Glu Thr Ile Arg Leu Arg Ser Cys
545                 550                 555                 560

Ala Arg Leu Thr Glu Leu Pro Cys Leu Gly Gln Leu His Ile Leu Arg
                565                 570                 575

His Leu His Ile Asp Gly Met Ser Gln Val Arg Gln Ile Asn Leu Gln
            580                 585                 590

Phe Tyr Gly Thr Gly Glu Val Ser Gly Phe Pro Leu Leu Glu Leu Leu
        595                 600                 605

Asn Ile Arg Arg Met Pro Ser Leu Glu Glu Trp Ser Glu Pro Arg Arg
    610                 615                 620

Asn Cys Cys Tyr Phe Pro Arg Leu His Lys Leu Leu Ile Glu Asp Cys
625                 630                 635                 640

Pro Arg Leu Arg Asn Leu Pro Ser Leu Pro Pro Thr Leu Glu Glu Leu
                645                 650                 655

Arg Ile Ser Arg Thr Gly Leu Val Asp Leu Pro Gly Phe His Gly Asn
            660                 665                 670

Gly Asp Val Thr Thr Asn Val Ser Leu Ser Ser Leu His Val Ser Glu
        675                 680                 685

Cys Arg Glu Leu Arg Ser Leu Ser Glu Gly Leu Leu Gln His Asn Leu
    690                 695                 700

Val Ala Leu Lys Thr Ala Ala Phe Thr Asp Cys Asp Ser Leu Glu Phe
705                 710                 715                 720
```

-continued

```
Leu Pro Ala Glu Gly Phe Arg Thr Ala Ile Ser Leu Glu Ser Leu Ile
                725                 730                 735

Met Thr Asn Cys Pro Leu Pro Cys Ser Phe Leu Leu Pro Ser Ser Leu
            740                 745                 750

Glu His Leu Lys Leu Gln Pro Cys Leu Tyr Pro Asn Asn Asn Glu Asp
        755                 760                 765

Ser Leu Ser Thr Cys Phe Glu Asn Leu Thr Ser Leu Ser Phe Leu Asp
    770                 775                 780

Ile Lys Asp Cys Pro Asn Leu Ser Ser Phe Pro Pro Gly Pro Leu Cys
785                 790                 795                 800

Gln Leu Ser Ala Leu Gln His Leu Ser Leu Val Asn Cys Gln Arg Leu
                805                 810                 815

Gln Ser Ile Gly Phe Gln Ala Leu Thr Ser Leu Glu Ser Leu Thr Ile
            820                 825                 830

Gln Asn Cys Pro Arg Leu Thr Met Ser His Ser Leu Val Glu Val Asn
        835                 840                 845

Asn Ser Ser Asp Thr Gly Leu Ala Phe Asn Ile Thr Arg Trp Met Arg
    850                 855                 860

Arg Arg Thr Gly Asp Asp Gly Leu Met Leu Arg His Arg Ala Gln Asn
865                 870                 875                 880

Asp Ser Phe Phe Gly Gly Leu Leu Gln His Leu Thr Phe Leu Gln Phe
                885                 890                 895

Leu Lys Ile Cys Gln Cys Pro Gln Leu Val Thr Phe Thr Gly Glu Glu
            900                 905                 910

Glu Glu Lys Trp Arg Asn Leu Thr Ser Leu Gln Ile Leu His Ile Val
        915                 920                 925

Asp Cys Pro Asn Leu Glu Val Leu Pro Ala Asn Leu Gln Ser Leu Cys
    930                 935                 940

Ser Leu Ser Thr Leu Tyr Ile Val Arg Cys Pro Arg Ile His Ala Phe
945                 950                 955                 960

Pro Pro Gly Gly Val Ser Met Ser Leu Ala His Leu Val Ile His Glu
                965                 970                 975

Cys Pro Gln Leu Cys Gln His Val Pro Gly Thr Phe Gly His Pro
            980                 985                 990


<210> SEQ ID NO 2
<211> LENGTH: 39
<212> TYPE: PRT
<213> ORGANISM: Artificial Sequence
<220> FEATURE:
<223> OTHER INFORMATION: ORF 156

<400> SEQUENCE: 2

Met Arg Phe Leu Pro Glu Val Ser Ala Cys Pro Trp His Ile Trp Ser
1               5                   10                  15

Ser Met Asn Ala Leu Ser Cys Val Ser Met Ser Leu Ala His Leu Val
            20                  25                  30

Ile His Glu Cys Pro Gln Pro
        35


<210> SEQ ID NO 3
<211> LENGTH: 39
<212> TYPE: PRT
<213> ORGANISM: Artificial Sequence
<220> FEATURE:
<223> OTHER INFORMATION: ORF 111
```

-continued

<400> SEQUENCE: 3

Met His Val Met Leu Tyr Ser Trp Ile Arg Arg Gly Arg Glu Asp Asp
1 5 10 15

Ser Gly Gly Ser Ile Arg Ile Thr His Tyr Tyr Gly Gln Phe Lys Leu
20 25 30

Lys Ala Gly Ala Asn Ser His
35

<210> SEQ ID NO 4
<211> LENGTH: 56
<212> TYPE: PRT
<213> ORGANISM: Artificial Sequence
<220> FEATURE:
<223> OTHER INFORMATION: ORF 87

<400> SEQUENCE: 4

Met Cys Tyr Ser Asp Arg Ser Ser Arg Val Val Phe Pro Ala Pro Pro
1 5 10 15

Asn Pro Thr Ile Glu His His Met His Ser Gly Ile Ile Glu Asn Lys
20 25 30

Asn Leu Lys Phe Ser Thr Glu Lys Cys Phe Val Ile Val Arg Arg Leu
35 40 45

Val His Lys Thr Glu Asn Val Lys
50 55

<210> SEQ ID NO 5
<211> LENGTH: 66
<212> TYPE: PRT
<213> ORGANISM: Artificial Sequence
<220> FEATURE:
<223> OTHER INFORMATION: ORF 71

<400> SEQUENCE: 5

Met Pro Leu Pro Thr Val Val Pro Lys Met Asp Pro His Pro Arg Gly
1 5 10 15

Ala Ser Trp Lys Lys Lys Thr Phe Gln Pro Arg Leu Gln Ser Lys Trp
20 25 30

Ile Asp Val Asn Met Leu Glu Gln Leu Trp Arg Ile Tyr Cys Gly Val
35 40 45

Asn Lys Leu Thr Leu Arg Gln Leu Asn Asn Thr Leu Arg Thr Phe Leu
50 55 60

Met Tyr
65

<210> SEQ ID NO 6
<211> LENGTH: 93
<212> TYPE: PRT
<213> ORGANISM: Artificial Sequence
<220> FEATURE:
<223> OTHER INFORMATION: ORF 49

<400> SEQUENCE: 6

Met Thr Lys Cys Ala Arg Asp Met Leu Thr Gln Leu Arg Ala Phe Met
1 5 10 15

Asp Asp Gln Met Cys Gln Gly His Ala Asp Thr Ser Gly Arg Lys Arg
20 25 30

Met Asp Ser Trp Ala Ser Asp Asp Val Gln Gly Ala Glu Gly Ala Glu
35 40 45

-continued

```
Ala Leu Gln Val Cys Arg Gln Tyr Leu Gln Val Trp Thr Ile Asn Asp
    50                  55                  60

Val Gln Asn Leu Lys Arg Ser Lys Val Ser Pro Leu Leu Phe Leu Phe
65                  70                  75                  80

Ala Gly Glu Gly Tyr Glu Leu Trp Thr Leu Ala Asp Leu
                85                  90


<210> SEQ ID NO 7
<211> LENGTH: 32
<212> TYPE: PRT
<213> ORGANISM: Artificial Sequence
<220> FEATURE:
<223> OTHER INFORMATION: ORF 7

<400> SEQUENCE: 7

Met Asp Arg His Leu Lys Ser Arg Ile Arg Phe Trp Phe Lys Gln Gln
1               5                   10                  15

Trp Pro Arg Gln Leu Asn Asn Thr Leu Arg Cys Lys Gln Ile Asp Ala
            20                  25                  30
```

We claim:

1. A new and distinct variety of banana plant, substantially as herein shown and described.

* * * * *

Significant difference based on chi-square?

| | |
|---|---|
| 'QCAV-4' vs. Grand Nain: | YES ($p < 0.0001$) |
| 'QCAV-4' vs. 'RGA2-5': | YES ($p < 0.0001$) |
| 'QCAV-4' vs. 'RGA2-2': | YES ($p < 0.01$) |
| 'QCAV-4' vs. 'RGA2-3': | NO |